(12) United States Patent
Sandhu et al.

(10) Patent No.: US 8,541,498 B2
(45) Date of Patent: Sep. 24, 2013

(54) LUBRICIOUS COATINGS FOR MEDICAL DEVICES

(75) Inventors: Shivpal S. Sandhu, Buckinghamshire (GB); Alan Rhodes, Reading (GB); Simon Jon Onis, Reading (GB)

(73) Assignee: Biointeractions Ltd., Reading, Berkshire (GB)

( * ) Notice: Subject to any disclaimer, the term of this patent is extended or adjusted under 35 U.S.C. 154(b) by 367 days.

(21) Appl. No.: 12/877,233

(22) Filed: Sep. 8, 2010

(65) Prior Publication Data

US 2012/0059111 A1    Mar. 8, 2012

(51) Int. Cl.
*C08L 39/06* (2006.01)
*C08F 226/10* (2006.01)

(52) U.S. Cl.
USPC ............ 524/518; 525/203; 526/263; 427/2.1; 427/2.24; 427/2.3

(58) Field of Classification Search
USPC ......... 524/548; 525/203; 526/263; 427/2.1, 427/2.24, 2.3
See application file for complete search history.

(56) References Cited

U.S. PATENT DOCUMENTS

| | | | |
|---|---|---|---|
| 3,429,852 A | 2/1969 | Skoultchi | |
| 3,620,733 A | 11/1971 | Steppan et al. | |
| 3,871,885 A | 3/1975 | Hertler | |
| 3,928,113 A | 12/1975 | Rosenberg | |
| 4,847,137 A | 7/1989 | Kellen et al. | |
| 4,973,493 A | 11/1990 | Guire | |
| 5,002,582 A | 3/1991 | Guire et al. | |
| 5,005,287 A | 4/1991 | Ritter | |
| 5,026,806 A | 6/1991 | Rehmer et al. | |
| 5,079,093 A | 1/1992 | Akashi et al. | |
| 5,263,992 A | 11/1993 | Guire | |
| 5,290,585 A | 3/1994 | Elton | |
| 5,391,414 A | 2/1995 | Doering et al. | |
| 5,441,488 A | 8/1995 | Shimura et al. | |
| 5,468,821 A | 11/1995 | Lucast et al. | |
| 5,509,899 A | 4/1996 | Fan et al. | |
| 5,603,991 A | 2/1997 | Kupiecki et al. | |
| 5,770,283 A | 6/1998 | Gosselin et al. | |
| 5,800,412 A | 9/1998 | Zhang et al. | |
| 5,919,563 A | 7/1999 | Parish, Jr. et al. | |
| 6,007,833 A | 12/1999 | Chudzik et al. | |
| 6,096,798 A | 8/2000 | Luthra et al. | |
| 6,287,285 B1 | 9/2001 | Michal et al. | |
| 6,406,687 B1 | 6/2002 | Luthra et al. | |
| 6,849,669 B1 | 2/2005 | Hodd et al. | |
| 7,459,489 B2 | 12/2008 | Lewandowski et al. | |
| 7,459,496 B2 | 12/2008 | Hsu et al. | |
| 7,544,381 B2 | 6/2009 | Kangas | |
| 7,682,648 B1 | 3/2010 | Ding et al. | |
| 7,691,476 B2 | 4/2010 | Finley | |
| 2001/0011165 A1 | 8/2001 | Engelson et al. | |
| 2002/0002353 A1 | 1/2002 | Michal et al. | |
| 2005/0147647 A1 | 7/2005 | Glauser et al. | |
| 2006/0210602 A1 | 9/2006 | Sehl et al. | |
| 2007/0078388 A1 | 4/2007 | Kangas | |
| 2007/0155907 A1 | 7/2007 | Zhao | |
| 2007/0197694 A1 | 8/2007 | Guha et al. | |
| 2008/0139689 A1 | 6/2008 | Huang et al. | |
| 2009/0041923 A1 | 2/2009 | Lin et al. | |
| 2009/0232871 A1 | 9/2009 | Hitz et al. | |
| 2009/0324666 A1 | 12/2009 | Krongauz et al. | |
| 2010/0049146 A1 | 2/2010 | Nielsen et al. | |

FOREIGN PATENT DOCUMENTS

| | | |
|---|---|---|
| EP | 0 166 998 A2 | 1/1986 |
| EP | 0 188 110 | 7/1986 |
| EP | 0 246 848 | 11/1987 |
| WO | 90/01344 A1 | 2/1990 |
| WO | 99/19004 A2 | 4/1999 |
| WO | 00/65915 A1 | 11/2000 |
| WO | 03/070792 A1 | 8/2003 |
| WO | 2004/020012 A1 | 3/2004 |
| WO | 2004/091685 A2 | 10/2004 |
| WO | 2006/034128 A2 | 3/2006 |
| WO | 2007/056338 | 5/2007 |
| WO | WO 2007/056338 A2 * | 5/2007 |

OTHER PUBLICATIONS

Czech, Studies on the photoreactive acrylic adhesive with high shrinkage resistance, Polish Journal of Chemical Technology, 6(4), 5-9 (2004).*

Nanjundan et al., "Homopolymer of 4-benzoylphenyl methacrylate and its copolymers with glycidyl methacrylate: synthesis, characterization, monomer reactivity ratios and application as adhesives", Reactive & Functional Polymers, 62(1):11-24 (Jan. 2005).

Czech; "Studies on the photoreactive acrylic adhesives with high shrinkage resistance", Polish Journal of Chemical Technology, 6(4), 5-9 (2004) (Abstract only).

PCT International Search Report and Written Opinion from Corresponding PCT Application No. PCT/GB2011/001291 (8 pages).

* cited by examiner

*Primary Examiner* — Robert D. Harlan

(74) *Attorney, Agent, or Firm* — Dardi & Herbert, PLLC.; Curtis B. Herbert

(57) ABSTRACT

Substrates may be coated with copolymers of N-vinyl pyrrolidinone and aryl ketones. Processes are described for making the copolymers at high molecular weight with the ketones randomly dispersed on the copolymer.

37 Claims, 1 Drawing Sheet

4-benzoylphenyl methacrylate

N-vinyl-2-pyrrolidone

LUBRICIOUS COATINGS FOR MEDICAL DEVICES

TECHNICAL FIELD OF THE INVENTION

The technical field, in general, relates to medical device coatings and polymers for the same.

BACKGROUND

Medical devices may benefit from coatings that enhance biocompatibility and other surface properties. The coatings provide desirable surface properties without sacrificing the mechanical properties of the underlying substrate.

SUMMARY

An embodiment of the invention is a copolymer of N-vinyl pyrrolidinone and diaryl ketone monomers. The diaryl ketone monomeric units are randomly dispersed through the length of the copolymer. In contrast, a conventional method of synthesis places the diaryl ketone mers in groups so that the copolymer is not formed. These copolymers have been discovered to provide coatings with desirable properties.

The copolymer of N-vinyl pyrrolidinone and diaryl ketone can be made in a water soluble form, with an average molecular weight of more than about 100,000, with at least about 60% by weight N-vinyl pyrrolidinone, and with no more than about 5% by weight diaryl ketone monomer. The water soluble nature of the copolymer contributes to hydrophilicity of coatings made with the copolymer. The molecular weight of more than about 100,000 provides performance characteristics that are distinct from lower molecular weight.

Another embodiment of the invention pertains to a coating comprising copolymer of N-vinyl pyrrolidinone and diaryl ketone monomers with the diaryl ketone monomeric units randomly dispersed through the length of the copolymer.

Another embodiment of the invention pertains to a method of making copolymer of N-vinyl pyrrolidinone and diaryl ketone monomers where the diaryl ketone monomeric units are randomly dispersed through the length of the copolymer. These copolymers have been discovered to provide coatings with desirable properties.

Another embodiment of the invention pertains to a method of making a coating comprising copolymer of N-vinyl pyrrolidinone and diaryl ketone monomers with the diaryl ketone monomeric units randomly dispersed through the length of the copolymer.

The diaryl ketones in the copolymer are activated to make covalent crosslinks to thereby form crosslinked layers. The water soluble nature of the copolymer contributes to the hydrophilicity of coatings made with the copolymer. The more than about 100,000 molecular weight of the copolymer provides significant control distances between crosslinks.

DETAILED DESCRIPTION OF PREFERRED EMBODIMENTS

A water soluble copolymer of N-vinyl pyrrolidinone (NVP) and monomers with diaryl ketone monomeric units randomly dispersed through the length of the copolymer is disclosed. The copolymer was synthesized with approaches described herein. The water soluble copolymer may be additionally crosslinked. In general, the copolymer or the crosslinked copolymer may be used as lubricious coatings on medical devices.

The term water soluble means that 1 L of water will dissolve at least 1 g of the polymer. The term polymer refers to a molecule composed of repeated subunits. The subunits are referred to as mers. The terms monomeric unit or monomer unit are used interchangeably with the term mer. The polymers may be formed by polymerization of monomers. The monomers undergo chemical reactions with each other to form covalent bonds. The monomers used may be the same or different. The term copolymer refers to a polymer derived from two or more monomeric units, as opposed to a homopolymer where only one monomer is used. The term random means that the probability of finding a given monomeric unit at any given site in the chain is substantially independent of the nature of the adjacent units. The term group indicates that the generically recited chemical entity (e.g., alkyl group) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents having heteroatom such as 3-ethoxylpropyl, 4-(N-ethylamino)butyl, 3-hydroxypentyl, 2-thiolhexyl, 1,2,3-tribromopropyl, and the like. However, as is consistent with such nomenclature, no substitution would be included within the term that would alter the fundamental bond structure of the underlying group.

Figure 1A:
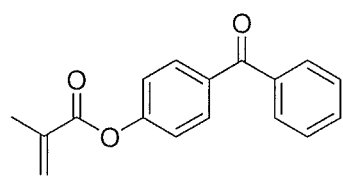
FIG. 1A depicts the structure of 4-benzoylphenyl methacrylate.
Figure 1B:
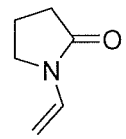
FIG. 1B depicts the structure of N-vinyl pyrrolidinone.
Figure 1C:
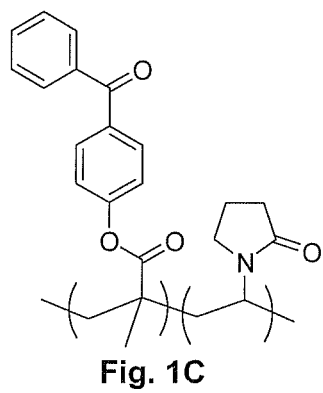
FIG. 1C depicts the polymerization of N-vinyl pyrrolidinone and 4-benzoylphenyl methacrylate.

An example of an aryl ketone is benzophenone, which is a diaryl ketone. FIG. 1A depicts the structure of NVP, FIG. 1B depicts the structure of 4-benzoylphenyl methacrylate, and FIG. 1C depicts the copolymer formed from the polymerization of these two monomeric units. Diaryl ketone is a group that has a carbonyl group in which the carbon of the carbonyl group is bound directly to two carbon atoms that are part of aromatic rings. For example, the simplest (monomeric)diaryl ketone is benzophenone, also called diphenyl ketone. Other diaryl ketones are, for example, acetophenone, anthraquinone, anthrone, and anthrone-like heterocycles, and their substituted derivatives. Additional diaryl ketones are 2-hydroxybenzophenone, 3-hydroxybenzophenone, 4-hydroxybenzophenone, 2,2'-dihydroxybenzophenone, 2,4-dihydroxybenzophenone, 3,4-dihydroxybenzophenone, 4,4'-dihydroxybenzophenone, 2,3,4-trihydroxybenzophenone, 2,4,4'-trihydroxybenzophenone, 2,2',4,4'-tetrahydroxybenzophenone, 2-aminobenzophenone, 3-aminobenzophenone, 4-aminobenzophenone, 3,4-diaminobenzophenone, 4,4'-diaminobenzophenone, 4-(bromomethyl)benzophenone, 2-benzoylbenzoic acid, 3-benzoylbenzoic acid, 4-benzoylbenzoic acid, 4-benzoylbenzoyl chloride, 4-isocyanatobenzophenone, benzophenone-3,3',4,4'-tetracarboxylic dianhydride, 3-bromo-2',5-dichloro-2-hydroxybenzophenone, 2-hydroxy-2',3,5-trichlorobenzophenone, 3-bromo-5-chloro-2-hydroxybenzophenone, 5-bromo-2'-chloro-2-hydroxybenzophenone, 4'-chloro-5-fluoro-2-hydroxybenzophenone, 2',5-dichloro-2-hydroxybenzophenone, 5-bromo-2-hydroxybenzophenone, 4-fluoro-4'-hydroxybenzophenone, 2-amino-4'-bromobenzophenone, 2-amino-5-chlorobenzophenone, 4-amino-3-nitrobenzophenone, 2'-chloro-2-hydroxy-4-methylbenzophenone, 2'-chloro-2-hydroxy-5-methylbenzophenone, 2-hydroxy-5-methylbenzophenone, 2-hydroxy-4-methoxybenzophenone, 2-amino-4-methylbenzophenone, benzoin, 4,4'-dimethoxybenzoin, 4-chlorobenzoin, benzyl 4-hydroxyphenyl ketone, benzyl 2,4-dihydroxyphenyl ketone, 2-phenyl-2',4',6'-trihydroxyacetophenone. The monomers may have an aryl ketone group or other pendant groups.

The copolymer may consist essentially of the NVP and aryl ketone monomeric units, or may further comprise additional monomers. In this context, the term essentially refers to having at least about 90% w/w of NVP in the copolymer, with the remaining 10% being the aryl ketones or hydrophilic mers. Embodiments include a water soluble copolymer with more than about 50% or about 60% w/w of NVP monomeric units and no more than 5% or 10% aryl ketone monomeric units; artisans will immediately appreciate that all the ranges and values within the explicitly stated ranges are contemplated. The copolymers may be prepared with less than 0.5% aryl ketone monomeric units (e.g., benzophenone); artisans will immediately appreciate that all the ranges and values within the explicitly stated ranges are contemplated, e.g., about 0.2% or from about 0.05% to about 0.25%.

In some embodiments the water soluble copolymer has no more than about 5% w/w of an aryl ketone (or diaryl ketone) monomeric unit; artisans will immediately appreciate that all the ranges and values within the explicitly stated ranges are contemplated, e.g., from about 1% to about 5% or less than about 0.5%. The molecular weight of the copolymer may be, for example, at least 100,000; artisans will immediately appreciate that all the ranges and values within the explicitly stated ranges are contemplated, e.g., from about 100,000 to about 1,500,000, or about 900,000 to about 1,200,000. The rest of the copolymer may be NVP, or the NVP may be present in a range of about 10% w/w to about 99% w/w, with other mers set forth herein providing the balance, e.g., at least 60% NVP monomeric units. Embodiments include coatings formed of such copolymers.

Monomers for the copolymer may have active centers comprising vinylic groups that form free radicals and undergo polymerization. Examples of active centers are acrylate groups and methacrylate groups. The monomers may have further substituents to form derivatives of acrylate and methacrylate. Examples of such substituents are hydroxyls and alkyls. Further monomers thus include methyl methacrylate, ethyl methacrylate, n-alky methacrylates, methyl ethyl acrylate, ethyl acrylate, n-alky acrylates, and hydroxyethlymethacrylate.

The monomer groups may have further substituent groups. Examples include poly(ethylene glycol) groups, poly(propylene glycol) groups, poly(alkylene oxide) groups, silyl groups, trimethoxysilyl groups, sulfonic acid groups, ammonium sulfatoethyl groups, methylpropanesulfonic acid groups, polyhexanide groups, and chlorhexidine groups. Further exemplary substituents include sulfate groups, sulfabetaine groups, phopshorylcholine groups, zwitterionic groups, 2-methacryloyloxyethyl phopshorylcholine (MPC), carboxylic acids, heparin, heparin methacrylate, alcohols, and hydroxyls. Further monomeric units are set forth in U.S. Pat. Nos. 6,007,833, 6,849,669, 7,138,541, and 7,459,489, which are hereby incorporated by reference herein for all purposes; in the case of conflict, the present specification controls.

The term alkyl, unless otherwise specified, refers to a saturated straight, branched, or cyclic hydrocarbon, and specifically includes, e.g., methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The alkyl group can be optionally substituted with any appropriate group, including but not limited to one or more groups selected from halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art.

All of these various groups may be optionally derivatized with substituent groups. Suitable substituent groups that may be present on such a "substituted" group include e.g. halogens such as fluoro, chloro, bromo and iodo; cyano; H, hydroxyl group; ester group; ether group; a carbamate, an oxo acid group, an oxo carbon group, an oxo carboxylic acid group, an oxo group, a ketone group; nitro; azido; sulfhydryl; alkanoyl e.g. $C_{1-6}$ alkanoyl group such as acetyl and the like; carboxamido; alkyl groups, alkenyl and alkynyl groups including groups having one or more unsaturated linkages; alkoxy groups having one or more oxygen linkages; aryloxy such as phenoxy; alkylthio groups; alkylsulfinyl groups; alkylsulfonyl groups; aminoalkyl groups such as groups having one or more N atoms; carbocyclic aryl; aryloxy such as phenoxy; aralkyl having 1 to 3 separate or fused rings; aralkoxy having 1 to 3 separate or fused rings; or a heteroaromatic, heterocyclic, or heteroalicyclic group having 1 to 4 separate or fused rings e.g., with one or more N, O or S atoms, e.g. coumarinyl, quinolinyl, pyridyl, pyrazinyl, pyrimidyl, furyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl. In some embodiments, the substituents may include groups that include O, S, Se; N, P, Si, C and have between 2 and about 150 atoms. In some embodiments, it is useful to limit the size of any substituent to, e.g., less than about 150, less than about 100, less than about 50, or less than about 20 atoms.

In some embodiments, suitable substituent groups include these and other N-containing compounds e.g., amines, amides, amidium ions, amine imides, amine oxides, aminium ions, aminonitrenes, nitrenes, aminoxides, nitriles, and nitrile imides. Other suitable substituent groups include these and other S-containing compounds, e.g., sulfonic acid, sulfate, sulfonates, sulfamic acids, sulfanes, sulfatides, sulfenamides, sulfenes, sulfenic acids, sulfenium ions, sulfenyl groups, sulfenylium ions, sulfenyl nitrenes, sulfenyl radicals, sulfides, sulfilimines, sulfimides, sulfimines, sulfinamides, sulfinamidines, sulfines, sulfinic acids, sulfinic anhydrides, sulfinimines, sulfinylamines, sulfolipids, sulfonamides, sulfonamidines, sulfonediimines, sulfones, sulfonic acids, sulfonic anhydrides, sulfonamides, sulfonium compounds, sulfonphthaleins, sulfonylamines, sulfoxides, sulfoximides, sulfoximines, sulfur diimides, thiols, thioacetals, thioaldehydes, thioaldehyde S-oxides, thioanhydrides, thiocarboxylic acids, thiocyanates, thioethers, thiohemiacetals, thioketones, thioketone S-oxides, thiolates, and thionylamines. In some embodiments, suitable substituent groups include these and other O-containing compounds, e.g., having the form ROH (alcohol), RCOOH (carboxylic acids), RCHO (aldehydes), RR'C=O (ketones), ROR' (ethers), and RCOOR' (esters), with the R denoting a bond or atomic element. In some embodiments, suitable substituent groups include these and other P-containing compounds, e.g., phosphanes, phosphanylidenes, phosphatidic acids, phosphazenes, phosphine oxides, phosphines, phosphinic acids, phosphinidenes, phosphinous acids, phosphoglycerides, phospholipids, phosphonic acids, phosphonitriles, phosphonium compounds, phosphonium ylides, phosphono, phosphorous acids, phosphoramides, and phosphoranes. Carbon is useful for making substituents and the number of carbons in a heteroatomic structure may be, e.g., between 1 and n−1 when between 2 and n atoms are used to form a substituent with, e.g., O, P, S, or N. In some embodiments, it is useful to limit the size of these substituents to, e.g., less than about 150, less than about 100, less than about 50, or less than about 20 atoms.

A variety of substituents are contemplated so that some potential combinations of claimed embodiments may be unstable or impractical to make. A person of ordinary skill in the art can select appropriate stable compounds within the disclosed genus of compounds based on the disclosure herein. Therefore, substituents generally are limited to those substituents that result in appropriate valence for the particular substituted element without forming a charged compound or a radical (except for titratable charged groups, stable zwitterionic forms and triplet neutral radicals with formal unpaired spins with full valencies), as can be conventionally determined by a person of ordinary skill in the art.

The copolymer is a copolymer comprised of N-vinyl pyrrolidinone (NVP) and monomers with an aryl ketone pendant group, with the aryl ketone monomeric units being randomly distributed in the copolymer. Mixing and conventional polymerization of monomeric NVP and monomeric aryl ketones is not effective to synthesize such a copolymer. It was discovered, however, that such a copolymer could be synthesized using approaches described herein. For example, dissolving the polymerization initiator in the NVP monomer was found to be helpful. in preparing the copolymer with randomly distributed aryl ketone monomeric units. Additionally, it was found to be helpful to dissolve the aryl ketone monomer in the NVP. But these approaches, alone or combined, were not sufficient to prepare the desired copolymer as indicted in Examples 2 and 4 below. The desired copolymer can be made, however, by adding these solutions in a controlled manner to a larger solution, with ongoing polymerization as illustrated in Examples 3 and 5 below. The copolymers thus formed were soluble in water and other aqueous solution sometimes with molecular weights of about 1,000,000. The copolymers could be made to provide coatings with unexpected and surprisingly favourable properties, including: thin, lubricious, and durable coatings.

More specifically, a 4-benzoylphenyl methacrylate (an aryl ketone monomeric unit) was synthesized (Example 1) and mixed in a solvent with NVP. An initiator was dissolved in NVP and added to the mixture of monomeric units. The initiator started polymerization but poly(4-benzoylphenyl methacrylate) polymer was produced instead of NVP-co-aryl ketone copolymer (Example 2). Accordingly, this approach did not work even when the initiator was dissolved in the NVP.

In contrast, in Example 3, the initiator was dissolved in NVP to form a first solution and the aryl ketone was dissolved in NVP in a second solution. A third solution of NVP in water was prepared, and heated. The first solution was added to the third to form a mixture. The second solution was slowly added dropwise to the mixture. A water soluble copolymer of poly(N-vinyl-2-pyrrolidinone-co-4-benzoylphenyl methacrylate) was formed. Further, a high molecular weight in excess of about 1,000,000 was achieved.

Similarly, Example 4 demonstrates how the formation of poly(N-vinyl-2-pyrrolidinone-co-4-benzoylphenyl methacrylate-co-methoxypolyethylene glycol 550 methacrylate) was not successful, even when the various components were dissolved in NVP and mixed. In this case, the methoxypolyethylene glycol 550 methacrylate polymerized with itself instead of making a copolymer. But poly(N-vinyl-2-pyrrolidinone-co-4-benzoylphenyl methacrylate-co-methoxypolyethylene glycol 550 methacrylate) was successfully made (Example 5) when the processes similar to the procedure described in Example 2 was adapted.

These approaches are generally suited to the formation of copolymer of N-vinyl pyrrolidinone (NVP) and monomers with an aryl ketone pendant group, as evidenced by numerous examples: poly(N-vinyl-2-pyrrolidinone-co-4-benzoylphenyl methacrylate) in Example 3; poly(N-vinyl-2-pyrrolidinone-co-4-benzoylphenyl methacrylate-co-methoxypolyethylene glycol 550 methacrylate) in Example 5; poly[N-vinyl-2-pyrrolidinone-co-4-benzoylphenyl methacrylate-co-(2-methacryloyloxy)ethyl dimethyl-(3-sulfopropyl) ammonium hydroxide] in Example 6; poly(N-vinyl-2-pyrrolidinone-co-4-benzoylphenyl methacrylate-co-(3-methacryloylamino)prop dimethyl-(3-sulfopropyl) ammonium hydroxide] in Example 7; poly(N-vinyl-2-pyrrolidinone-co-4-benzoylphenyl methacrylate-co-2-methacryoyloxyethyl phosphorylcholine) in Example 8; poly (N-vinyl-2-pyrrolidinone-co-4-benzoylphenyl methacrylate-co-ammonium sulfatoethyl methacrylate) in Example 9; poly (N-vinyl-2-pyrrolidinone-co-4-benzoylphenyl methacrylate-co-acrylic acid) in Example 10; poly(N-vinyl-2-pyrrolidinone-co-4-benzoylphenyl methacrylate-co-dimethylaminoethyl methacrylate) in Example 11; poly(N-vinyl-2-pyrrolidinone-co-4-benzoylphenyl methacrylate-co-2-hydroxyethyl methacrylate) in Example 12 and poly(N-vinyl-2-pyrrolidinone-co-4-benzoylphenyl methacrylate-co-polyhexanide methacrylate) in Example 13. These copolymers and derivatives thereof that further comprise additional groups or substitutions are embodiments of inventions, as are coatings of the same. Azobisisobutyronitrile (AIBN) is an initiator for polymerization of the copolymer; others are also suitable, as is known to artisans.

Another embodiment of the invention is a coating or a layer comprising a copolymer as set forth herein, for instance, a copolymer of N-vinyl pyrrolidinone (NVP) and monomers with an aryl ketone pendant group. Such copolymers can form lubricious and tough coatings. Example 3 describes synthesis of such a copolymer. Polymers made from the same precursors, however, did not provide these characteristics; the properties of a coating of the polymer of Example 2 were observed to be quite poor compared to the copolymer of Example 3 (see Examples 14 and 15).

Moreover, the copolymer coatings had excellent flexibility and were highly lubricious. The friction coefficient can be defined as the force required to move a sample through a clamp of constant force divided by the force that is applied by the clamp. For example, if the force required to pull a sample through a clamp, which has a force of 400 g applied to it, is 100 g, then the friction coefficient will be 0.25. Friction coefficients for coatings of the copolymers range from 0.5 to 0.005 depending on the substrate used. The coating reduces the friction coefficient by about 50 to about 99.5% compared with the uncoated sample; artisans will immediately appreciate that all the ranges and values within the explicitly stated ranges are contemplated, e.g, a reduction of about 60%, about 90%, or from about 80% to about 99.5%.

Embodiments include a coating comprising covalently crosslinked copolymers as set forth herein, the coating being hydrophilic, highly flexible, and durable. Highly flexible means that a coating of about 50 to about 200 µm thickness applied to a substrate will not crack as observed by the naked eye. The contact angle is the angle at which a liquid/vapor interface meets a solid surface, with lower contact angles representing a more hydrophilic (wettable) surface. Typical contact angles for water on surfaces coated with the present invention are between about 0° and about 30°; artisans will immediately appreciate that all the ranges and values within the explicitly stated ranges are contemplated, e.g, from about 0.1 to about 20°. Durability may be assessed by dying a coated substrate and then subjecting the coated article to a wet abrasion test. For example, by rubbing the wet coated article between the index finger and thumb using firm pressure for at least 20 cycles. If the dye does not fade, or the coating re-dyes to a similar intensity, then the coating passes the durability assessment. If the dye fades and does not re-dye, then the coating has not linked sufficiently and will delaminate from the substrate (as in Example 14).

A coating material is formed on a substrate. A substrate generally presents a surface onto which the coating material can be deposited, and the substrate may comprise a plurality of layers in which the surface relates to an upper most layer. The substrate surface can be treated to prepare the surface for adhesion of the coating material. Prior to preparation of the surface, the surface can be cleaned and/or smoothed as appropriate. Suitable substrate surfaces can comprise any reasonable material. Some substrates of particular interest include, for example, stainless steel, metals, nitinol, engineering polymers, polyethylene, polypropylene, polytetrafluoroethylene, polyurethane, polyamide, polyether block amide, inorganic materials, polymer substrates, such as organic polymers, composites thereof and combinations thereof across a surface and/or in layers of the substrate. The substrate may be a surface of a medical device, e.g., a surface exposed to blood and/or for temporary or permanent use inside a body. Examples of such medical devices are a stent, a guidewire, a pacemaker lead, a catheter, a medical balloon, a nasogastric feeding tube, a PICC line, and an endotracheal tube. Catheters may be, for example, a urinary catheter, an infusion catheter, and a drainage catheter. The term medical device as used herein is broad and includes medical diagnostic devices, for example, surfaces exposed to a biological sample for a diagnostic purpose.

In general, any suitable coating process can be used to deliver the copolymer to a substrate. Suitable coating approaches can include, for example, spin coating, spray coating, dip coating, painting, and casting. The aryl ketones may be activated after the copolymer is present on the substrate to promote crosslinking of the copolymers with each other to form a covalently crosslinked matrix. Light-based activation may be used, or other suitable means, e.g., heat. The coating material can be applied in multiple coating steps to provide greater control over the coating process. For example, multiple spin coatings can be performed to yield an ultimate coating thickness desired. The heat processing described below can be applied after each coating step or after a plurality of coating steps. Solvents for the copolymers in the coating process may be aqueous or alcoholic or a mixture thereof. Examples of alcohol include methanol, ethanol, and 2-propanol. Further solvents are water, dimethylsulfoxide, tetrahydrofuran, and dichloromethane. The method may comprise evaporating the solvent and drying the layer at a temperature ranging from about 15 to about 80° C.; artisans will immediately appreciate that all the ranges and values within the explicitly stated ranges are contemplated. The solvent may be aqueous, a term that means a solvent that is at least 10% v/v water, with the balance of the solvent being liquids miscible with the water. The solvent may consist essentially of water and/or alcohol, with the term essentially, in this context, meaning that the liquid phase of the solvent is at least 90% v/v water or alcohol and the balance of the liquid phase does not substantially interfere with the coating process.

The thickness of the coating generally can be a function of the coating process that is chosen. In some embodiments, the coating materials can have an average thickness of between about 1 µm and about 1 mm; artisans will immediately appreciate that all the ranges and values within the explicitly stated ranges are contemplated, e.g., about 10 µm to about 200 µm, or about 5 to about 20 µm.

Copolymers of N-vinyl pyrrolidinone (NVP) and monomers with an aryl ketone pendant group were made into effective coatings on a variety of substrates, including polyurethane (Examples 15 and 16), polyether block polymers (Example 17), polyamide (Example 18), and stainless steel (Example 19). The coatings were excellent and were flexible, durable, lubricious, and hydrophilic.

EXAMPLES

Example 1

Synthesis of 4-benzoylphenyl methacrylate

To a 100 mL round-bottomed flask equipped with a magnetic stirrer bar and an addition funnel was added 4-hydroxybenzophenone (1 g, 5.04 mmol) and $CH_2Cl_2$ (35 mL). The mixture was cooled to 0° C. and methacryloyl chloride (0.39 mL, 4.04 mmol) was added in one portion. After 30 minutes, triethylamine (0.7 mL, 5.04 mmol) dissolved in $CH_2Cl_2$ (10 mL) was added dropwise over 30 minutes. The reaction mixture was allowed to stir for a further 1 hour at 0° C. and then at room temperature for 3 hours. After this time, the organic mixture was washed with 0.1% NaOH (3×100 mL) and water (5×100 mL). The combined organic layers were dried over $MgSO_4$ and then concentrated in vacuo to afford a crude product. The crude product was purified by column chromatography (100% $CH_2Cl_2$) to provide the compound as a white solid (yield=75%, 1 g).

Example 2

Failed Synthesis of poly(N-vinyl-2-pyrrolidinone-co-4-benzoylphenyl methacrylate)

This Example demonstrates that merely combining a mixture of precursors does not provide for synthesis of poly(N-vinyl-2-pyrrolidinone-co-4-benzoylphenyl methacrylate). Instead, it results in a varied a mixture of polymers, apparently as a result of varied precursor reactivity ratios. In this case, poly(4-benzoylphenyl methacrylate) is apparently produced as evidenced by the resultant precipitates.

To a 250 mL conical flask equipped with a magnetic stirrer bar was added N-vinyl-2-pyrrolidinone (NVP) (30 g), 4-benzoylphenyl methacrylate (0.1 g) and deionized water (70 mL). The mixture was purged with $N_2$ for 20 minutes whilst being heated to 70° C. After this time, azobisisobutyronitrile (AIBN) (0.1 g dissolved in NVP, 2 mL) was added in one portion to initiate polymerization. After approximately 5 minutes the solution became cloudy and insoluble precipitates formed as a result of poly(4-benzoylphenyl methacrylate) precipitating out of solution.

Example 3

Synthesis of poly(N-vinyl-2-pyrrolidinone-co-4-benzoylphenyl methacrylate)

To a 250 mL conical flask equipped with a magnetic stirrer bar was added NVP (30 g) and deionized water (70 mL). The mixture was purged with $N_2$ for 20 minutes whilst being heated to 70° C. After this time, AIBN (0.1 g dissolved in NVP, 2 mL) was added in one portion. About 8 minute after the addition of AIBN, 4-benzoylphenyl methacrylate (0.1 g dissolved in NVP, 2 mL) was added dropwise over a period of 10 minutes. Polymerization was carried out for 1 hour, after which time the viscous mixture was allowed to cool to room temperature and then dissolved in water (150 mL). The resultant polymer solution was clear, with no evidence of poly(-benzoylphenyl methacrylate) precipitation. The polymer solution was dialyzed against water (10 L) for 16 h and then freeze dried to afford the title polymer as a white solid (yield=32 g). Gel permeation chromatography (GPC) was carried out on the white solid using a Perkin-Elmer Series 200 GPC system equipped with PL-AQUAGEL-OH 40 and PL-AQUAGEL-OH 50 columns (300×7.5 mm), a PL-AQUA-GEL 5 μm guard column and a refractive index (RI) detector. Molecular weights were determined relative to narrow poly(ethylene oxide)/poly(ethylene glycol) standards (Varian, Inc) using a mobile phase consisting of 0.02% $NaN_3$ in water at a flow rate of 1.0 mL/min at 30° C. with a sample injection of 50 μL. Typically, molecular weights in the 1,000,000 $gmol^{-1}$ range were measured.

Example 4

Failed Synthesis of poly(N-vinyl-2-pyrrolidinone-co-4-benzoylphenyl methacrylate-co-methoxypolyethylene glycol 550 methacrylate)

To a 250 mL conical flask equipped with a magnetic stirrer bar was added NVP (27 g), methoxypolyethylene glycol 550 methacrylate (MPEG 550 methacrylate) (6 g) and deionised water (100 mL). The mixture was purged with $N_2$ for 20 minutes whilst being heated to 70° C. After this time, AIBN (0.1 g dissolved in NVP, 2 mL) was added in one portion to initiate Polymerization. The solution became viscous within 5 minutes and a gel had formed within 8 minutes so that 4-benzoylphenyl methacrylate could not be added. The reaction was terminated by the addition of deionised water (150 mL). The gelled polymer was dialyzed against water (10 L) for 16 h and then freeze dried to afford 5 g of product. The polymeric product was insoluble in water, ethanol, dimethyl sulfoxide, dimethylformamide and mixtures thereof, indicating that a cross-linked product had been afforded. Evidently, the MPEG 550 methacrylate had homo-polymerized and, as a result of residual cross-linker present in the monomer, had formed an insoluble cross-linked gel.

The polymer was characterised by infrared spectroscopy using a Perkin-Elmer Paragon 1000 FT-IR spectrometer. Samples were recorded as a thin film. The absence of a C=O (amide) absorption at around 1650 $cm^{-1}$ indicated that no NVP had been incorporated into the polymer.

Example 5

Synthesis of poly(N-vinyl-2-pyrrolidinone-co-4-benzoylphenyl methacrylate-co-methoxypolyethylene glycol 550 methacrylate)

To a 250 mL conical flask equipped with a magnetic stirrer bar was added NVP (27 g) and deionised water (100 mL). The mixture was purged with $N_2$ for 20 minutes whilst being heated to 70° C. After this time, AIBN (0.1 g dissolved in NVP, 2 mL) was added in one portion. About 8 minutes after the addition of AIBN, 4-benzoylphenyl methacrylate (0.1 g dissolved in NVP, 2 mL) was added dropwise over a period of 10 minutes. Careful control over the rate and time of MPEG 550 methacrylate addition ensured the monomer did not homo-polymerize and did not cross-link to form a gel. Then, MPEG 550 methacrylate (6 g) containing 4-benzoylphenyl methacrylate (0.03 g) (dissolved in NVP, 1 mL) was added dropwise over a period of 10 minutes. Polymerization was carried out for 1 hour, whilst maintaining the reaction temperature between 70-75° C. After this time, the reaction was terminated by the addition of water (150 mL). The polymer solution was dialyzed against water (10 L) for 16 h and then freeze dried to afford the title polymer as a white solid (yield=30 g).

FT-IR analysis of the white solid revealed the presence of a strong absorption at around 1650 $cm^{-1}$, which was attributed to the C=O (amide) of the polymeric NVP. An absorption at around 1100 $cm^{-1}$ provided evidence for the presence of the polyethylene glycol unit (C—O—C).

Example 6

Synthesis of poly[N-vinyl-2-pyrrolidinone-co-4-benzoylphenyl methacrylate-co-(2-methacryloyloxy)ethyl dimethyl-(3-sulfopropyl)ammonium hydroxide]

Monomer2-(Methacryloyloxy)ethyl]dimethyl-(3-sulfopropyl)ammonium hydroxide (MEDSAH) was polymerised with NVP and 4-benzoylphenyl methacrylate following the procedure as described in Example 5 except that MEDSAH (6 g) was dissolved in water (10 mL) containing 4-benzoylphenyl methacrylate (0.03 g) (dissolved in NVP, 1 mL). The yield of the title polymer was 29 g.

FT-IR analysis revealed the presence of a strong absorption at around 1650 $cm^{-1}$, which was attributed to the C=O (amide) of the polymeric NVP and absorptions due to S=O at around 1200 $cm^{-1}$ and 1000 $cm^{-1}$ from the MEDSAH.

Example 7

Synthesis of poly(N-vinyl-2-pyrrolidinone-co-4-benzoylphenyl methacrylate-co-(3-methacryloylamino)propyl dimethyl-(3-sulfopropyl)ammonium hydroxide]

Monomer3-(Methacryloylamino)propyl]dimethyl-(3-sulfopropyl)ammonium hydroxide (MPDSAH) was polymerised with NVP and 4-benzoylphenyl methacrylate following the procedure as described in Example 6. The yield of the title polymer was 29 g.

FT-IR analysis revealed the presence of a strong absorption at around 1650 $cm^{-1}$, which was attributed to the C=O (amide) of the polymeric NVP and absorptions due to S=O at around 1200 $cm^{-1}$ and 1000 $cm^{-1}$ from the MPDSAH.

Example 8

Synthesis of poly(N-vinyl-2-pyrrolidinone-co-4-benzoylphenyl methacrylate-co-2-methacryoyloxy-ethyl phosphorylcholine)

Monomer 2-Methacryloyloxyethyl phopshorylcholine (MPC) was polymerised with NVP and 4-benzoylphenyl methacrylate following the procedure as described in Example 6. The yield of the title polymer was 25 g.

FT-IR analysis revealed absorptions at around 950, 1080 and 1260 $cm^{-1}$, which were attributed to the phosphate group of MPC and a strong absorption at around 1650 cm$^1$, which was attributed to the C=O (amide) of the polymeric NVP.

Example 9

Synthesis of poly(N-vinyl-2-pyrrolidinone-co-4-benzoylphenyl methacrylate-co-ammonium sulfatoethyl methacrylate)

Ammonium sulfatoethyl methacrylate (SEM) was polymerised with NVP and 4-benzoylphenyl methacrylate following the procedure as described in Example 6. The yield of the title polymer was 28 g.

Example 10

Synthesis of poly(N-vinyl-2-pyrrolidinone-co-4-benzoylphenyl methacrylate-co-acrylic acid)

Acrylic acid (sodium salt) was polymerised with NVP and 4-benzoylphenyl methacrylate following the procedure as described in Example 6. Once polymerised, the pH was reduced to ~3 to form the free acid. The yield of the title polymer was 26 g.

Example 11

Synthesis of poly(N-vinyl-2-pyrrolidinone-co-4-benzoylphenyl methacrylate-co-dimethylaminoethyl methacrylate)

Dimethylaminoethyl methacrylate was polymerised with NVP and 4-benzoylphenyl methacrylate following the procedure as described in Example 5. The yield of the title polymer was 29 g.

Example 12

Synthesis of poly(N-vinyl-2-pyrrolidinone-co-4-benzoylphenyl methacrylate-co-2-hydroxyethyl methacrylate)

2-hydroxyethyl methacrylate (HEMA) was polymerised with NVP and 4-benzoylphenyl methacrylate following the procedure as described in Example 5 The yield of the title polymer was 30 g.

Example 13

Synthesis of poly(N-vinyl-2-pyrrolidinone-co-4-benzoylphenyl methacrylate-co-polyhexanide methacrylate)

Polyhexanide methacrylate was polymerised with NVP and 4-benzoylphenyl methacrylate following the procedure as described in Example 6. The yield of the title polymer was 23 g.

Example 14

Coating of poly(urethane) tube with polymer from Example 2

The polymer prepared in Example 2 was dissolved in a mixture of isopropyl alcohol (IPA)/water to give a final polymer concentration of 3% w/v. A clean poly(urethane) tube was then immersed into the coating solution and left for approximately 30 seconds. After this time, the tube was slowly withdrawn from the solution and allowed to dry at room temperature for at least 10 minutes. Once dry, the coated poly(urethane) tube was exposed to a UVASPOT 1000 F UV lamp for 3 minutes. Upon exposure to water, the coating was easily delaminated from the surface indicating that no chemical cross-linking had occurred.

Example 15

Coating of poly(urethane) tube with co-polymer from Example 3

The co-polymer prepared in Example 3 was dissolved in a mixture of IPA/water to give a final polymer concentration of 3% w/v. A clean poly(urethane) tube was then immersed into the coating solution and left for approximately 30 seconds. After this time, the tube was slowly withdrawn from the solution and allowed to dry at room temperature for at least 10 minutes. Once dry, the coated poly(urethane) tube was exposed to a UVASPOT 1000 F UV lamp for 3 minutes to afford a thin, durable, cross-linked coating, which upon exposure to water became highly lubricious.

Example 16

Coating of poly(urethane) tube with co-polymer from Example 5

The co-polymer prepared in Example 5 was dissolved in a mixture of IPA/water to give a final polymer concentration of 3% w/v. A clean poly(urethane) tube was then immersed into the coating solution and left for approximately 30 seconds. After this time, the tube was slowly withdrawn from the solution and allowed to dry at room temperature for at least 10 minutes. Once dry, the coated poly(urethane) tube was exposed to a UVASPOT 1000 F UV lamp for 3 minutes to afford a thin, durable, cross-linked coating, which upon exposure to water became highly lubricious. The coating also exhibited excellent flexibility.

Example 17

Coating of PEBAX tube with co-polymer from Example 5

The co-polymer prepared in Example 5 was dissolved in a mixture of IPA/water to give a final polymer concentration of 3% w/v. A clean PEBAX tube was then immersed into the coating solution and left for approximately 30 seconds. After this time, the tube was slowly withdrawn from the solution and allowed to dry at room temperature for at least 10 minutes. Once dry, the coated PEBAX tube was exposed to a UVASPOT 1000 F UV lamp for 3 minutes to afford a thin, durable, cross-linked coating, which upon exposure to water became highly lubricious. The coating also exhibited excellent flexibility. PEBAX is a trade name for a block copolymer obtained by polycondensation of a carboxylic acid polyamide (PA6, PA11, PA12) with an alcohol termination polyether (PTMG, PEG).

Example 18

Coating of poly(amide) tube with co-polymer from Example 5

The co-polymer prepared in Example 5 was dissolved in a mixture of IPA/water to give a final polymer concentration of 3% w/v. A clean poly(amide) tube was then immersed into the coating solution and left for approximately 30 seconds. After this time, the tube was slowly withdrawn from the solution and allowed to dry at room temperature for at least 10 minutes. Once dry, the coated poly(amide) tube was exposed to a UVASPOT 1000 F UV lamp for 3 minutes to afford a thin, durable, cross-linked coating, which upon exposure to water became highly lubricious. The coating also exhibited excellent flexibility.

Example 19

Coating of stainless steel guidewire with co-polymer from Example 5

A commercially available polyester, such as DYNAPOL® L490, was first dissolved in THF at a concentration of 3% w/v. A clean stainless steel guidewire was then immersed into the solution and left for approximately 30 seconds. After this time, the guidewire was slowly withdrawn from the solution and dried in an oven at 60° C. for 30 minutes to afford a polyester coated guidewire.

The co-polymer prepared in Example 5 was dissolved in a mixture of IPA/water to give a final polymer concentration of 3% w/v. The polyester coated guidewire was then immersed into the coating solution and left for approximately 30 seconds. After this time, the tube was slowly withdrawn from the solution and allowed to dry at room temperature for at least 10 minutes. Once dry, the coated guidewire was exposed to a UVASPOT 1000 F UV lamp for 3 minutes to afford a thin, durable, cross-linked coating, which upon exposure to water became highly lubricious. The coating also exhibited excellent flexibility.

Further Disclosure

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

A coating on a medical device comprising hydrophilic layer comprising copolymers covalently crosslinked by photoinitiation of diaryl ketones pendant on the copolymers, with the copolymers, before photoinitiation, being polymerized from a plurality of monomers comprising N-vinyl pyrrolidinone and diaryl ketone vinyl monomer, having a weight average molecular weight of more than about 100,000, at least about 60% by weight N-vinyl pyrrolidinone, no more than about 5% by weight of diaryl ketone monomer that provides the pendant diaryl ketones, and a random distribution of the diaryl ketones.

An isolated set of polymers comprising copolymers polymerized from monomers comprising N-vinyl pyrrolidinone monomer and a diaryl ketone vinyl monomer, with the copolymers having a weight average molecular weight of more than about 100,000, at least about 60% by weight N-vinyl pyrrolidinone, no more than about 5% by weight diaryl ketone monomer, and a random distribution of the diaryl ketone in the copolymer.

A method of coating a medical device comprising exposing a medical device to copolymers having a weight average molecular weight of more than about 100,000, at least about 60% by weight N-vinyl pyrrolidinone, diaryl ketone monomer present at no more than about 5% by weight, and a random distribution of the diaryl ketone in the copolymer, and an ultraviolet source to activate the benzophenone to form crosslinks to create a covalently crosslinked layer on a surface of the medical device.

A process of making a copolymer comprising preparing a solution of N-vinyl pyrrolidinone in aqueous solution, adding a free radical polymerization initiator dissolved in N-vinyl pyrrolidinone to the solution, adding a aryl ketone vinyl monomer dissolved in N-vinyl pyrrolidinone to the solution, and polymerizing the monomers to form a random copolymer of the N-vinyl pyrrolidinone and the diaryl ketone monomer.

A copolymer comprising hydrophilic monomeric units and an aryl and/or diaryl ketone monomeric units, and a polyethylene backbone, wherein the copolymers have a weight average molecular weight of more than about 100,000, at least about 60% by weight of the hydrophilic monomeric units, no more than about 5% by weight diaryl ketone monomeric units, and a random distribution of the diaryl ketone monomeric units along the polyethylene backbone of the copolymer.

A process of making a copolymer comprising preparing a solution of a hydrophilic monomer in aqueous solution, adding a free radical polymerization initiator dissolved in the hydrophilic monomer to the solution, adding a diaryl ketone monomer dissolved in the hydrophilic monomer to the solution, and polymerizing the monomers to form a random copolymer of the hydrophilic monomer and the diaryl ketone monomer.

A hydrophilic coating on a medical device comprising polyethylene copolymers covalently crosslinked by diaryl ketones pendant on the copolymers, wherein the copolymer comprises hydrophilic monomeric units and diaryl ketone vinyl monomeric units, having an average molecular weight of more than about 100,000, at least about 60% by weight of the hydrophilic monomeric units, no more than about 5% by weight of diaryl ketone monomeric units that provides the pendant diaryl ketones, and a random distribution of the diaryl ketones along the polyethylene backbone.

A method of coating a medical device comprising exposing a medical device to copolymers having a weight average molecular weight of more than about 100,000, at least about 60% by weight N-vinyl pyrrolidinone, diaryl ketone monomer present at no more than about 5% by weight, and a random distribution of the diaryl ketone in the copolymer, and activating the diaryl ketone in the copolymer to form crosslinks to create a covalently crosslinked layer on a surface of the medical device.

A medical device comprising a copolymer or a coating as set forth herein, which medical device may include a medical device as set forth herein. A method, copolymer, coating, or process wherein (i) a coating of the copolymer has a friction coefficient of no more than about 0.2 or reduces a friction coefficient by more than about 50%; artisans will immediately appreciate that all the ranges and values within the explicitly stated ranges are contemplated and/or (ii) wherein the diaryl ketone is benzophenone and/or (iii) wherein the diaryl ketone monomer comprises a methacrylate group or an acrylate group and/or (iv) wherein the diaryl ketone of the copolymers is selected from the group consisting of 2-hydroxybenzophenone, 3-hydroxybenzophenone, 4-hydroxybenzophenone, 2,2'-dihydroxybenzophenone, 2,4-dihydroxybenzophenone, 3,4-dihydroxybenzophenone, 4,4'-dihydroxybenzophenone, 2,3,4-trihydroxybenzophenone, 2,4,4'-trihydroxybenzophenone, 2,2',4,4'-tetrahydroxybenzophenone, 2-aminobenzophenone, 3-aminobenzophenone, 4-aminobenzophenone, 3,4-diaminobenzophenone, 4,4'-diamonibenzophenone, 4-(bromomethyl)benzophenone, 2-benzoylbenzoic acid, 3-benzoylbenzoic acid, 4-benzoylbenzoic acid, 4-benzoylbenzoyl chloride, 4-isocyanatobenzophenone, benzophenone-3,3',4,4'-tetracarboxylic dianhydride, 3-bromo-2',5-dichloro-2-hydroxybenzophenone, 2-hydroxy-2',3,5-trichlorobenzophenone, 3-bromo-5-chloro-2-hydroxybenzophenone, 5-bromo-2'-chloro-2-hydroxybenzophenone, 4'-chloro-5-fluoro-2-hydroxybenzophenone, 2',5-dichloro-2-hydroxbenzophenone, 5-bromo-2-hydroxybenzophenone, 4-fluoro-4'-hydroxybenzophenone, 2-amino-4'-bromobenzophenone, 2-amino-5-chlorobenzophenone, 4-amino-3-nitrobenzophenone, 2'-chloro-2-hydroxy-4-methylbenzophenone, 2'-chloro-2-hydroxy-5-methylbenzophenone, 2-hydroxy-5-methylbenzophenone, 2-hydroxy-4-methoxybenzophenone, 2-amino-4-methylbenzophenone, benzoin, 4,4'-dimethoxybenzoin, 4-chlorobenzoin, benzyl 4-hydroxyphenyl ketone, benzyl 2,4-dihydroxyphenyl ketone, 2-phenyl-2',4',6'-trihydroxyacetophenone and/or (v) wherein the diaryl ketone monomer comprises a polymerizable group selected from the group consisting of acrylate groups, methacrylate groups, and methylmethacrylate groups and/or (vi) wherein the plurality of monomers further comprises one or more monomers selected from the group consisting of poly(ethylene glycol) methacrylate, polypropylene glycol) methacrylate, poly(ethylene glycol) methyl ether methacrylate, poly(ethylene glycol) ethyl ether methacrylate, 3-trimethoxysilyl propyl methacrylate, vinyl sulfonic acid (sodium salt), ammonium sulfatoethyl methacrylate, 2-acryloylamido-2-methylpropanesulfonic acid monomer, [2-(methacryloyloxy)ethyl]dimethyl-(3-sulfopropyl) ammonium hydroxide (MEDSAH), [3-(methacryloamino)propyl] dimethyl-(3-sulfopropyl)ammonium hydroxide (MPDSAH), 2-methacryloyloxyethyl phopshorylcholine (MPC), acrylic acid (sodium salt), dimethylaminoethyl methacrylate, 2-hydroxyethyl methacrylate (HEMA), polyhexanide methacrylate and chlorhexidine methacrylate and/or (vii) wherein the plurality of monomers further comprises a monomer that comprises a polyethylene glycol pendant group and/or (viii) wherein the plurality of monomers further comprises a monomer that comprises a pendant group terminating in a sulfonate group and/or (ix) wherein the plurality of monomers further comprises a monomer that comprises a silyl pendant group and/or (x) 1 wherein the plurality of monomers further comprise a monomer that comprises a zwitterionic group and/or (xi) wherein the plurality of monomers further comprise a monomer that comprises a hydroxyl group and/or (xii) wherein the copolymers, before photoinitiation, consist essentially of the polymerization product of the N-vinyl pyrrolidinone and the diaryl ketone monomer.

The invention claimed is:

1. A coating on a medical device comprising
   a hydrophilic layer comprising copolymers covalently crosslinked by photoinitiation of diaryl ketones pendant on the copolymers,
   with the copolymers, before photoinitiation, being polymerized from a plurality of monomers comprising N-vinyl pyrrolidinone and diaryl ketone vinyl monomer, having a weight average molecular weight of more than about 100,000, at least about 60% by weight N-vinyl pyrrolidinone, no more than about 5% by weight of diaryl ketone monomer that provides the pendant diaryl ketones, and a random distribution of the diaryl ketones, wherein the coating has a friction coefficient of no more than about 0.2.

2. The coating of claim 1 wherein the diaryl ketone is benzophenone.

3. The coating of claim 1 wherein the diaryl ketone monomer comprises a methacrylate group or an acrylate group.

4. The coating of claim 1 wherein the diaryl ketone of the copolymers is selected from the group consisting of 2-hydroxybenzophenone, 3-hydroxybenzophenone, 4-hydroxybenzophenone, 2,2'-dihydroxybenzophenone, 2,4-dihydroxybenzophenone, 3,4-dihydroxybenzophenone, 4,4'-dihydroxybenzophenone, 2,3,4-trihydroxybenzophenone, 2,4,4'-trihydroxybenzophenone, 2,2',4,4'-tetrahydroxybenzophenone, 2-aminobenzophenone, 3-aminobenzophenone, 4-aminobenzophenone, 3,4-diaminobenzophenone, 4,4'-diamonibenzophenone, 4-(bromomethyl)benzophenone, 2-benzoylbenzoic acid, 3-benzoylbenzoic acid, 4-benzoylbenzoic acid, 4-benzoylbenzoyl chloride, 4-isocyanatobenzophenone, benzophenone-3,3',4,4'-tetracarboxylic dianhydride, 3-bromo-2',5-dichloro-2-hydroxybenzophenone, 2-hydroxy-2',3,5-trichlorobenzophenone, 3-bromo-5-chloro-2-hydroxybenzophenone, 5-bromo-2'-chloro-2-hydroxybenzophenone, 4'-chloro-5-fluoro-2-hydroxybenzophenone, 2',5-dichloro-2-hydroxybenzophenone, 5-bromo-2-hydroxybenzophenone, 4-fluoro-4'-hydroxybenzophenone, 2-amino-4'-bromobenzophenone, 2-amino-5-chlorobenzophenone, 4-amino-3-nitrobenzophenone, 2'-chloro-2-hydroxy-4-methylbenzophenone, 2'-chloro-2-hydroxy-5-methylbenzophenone, 2-hydroxy-5-methylbenzophenone, 2-hydroxy-4-methoxybenzophenone, 2-amino-4-methylbenzophenone, benzoin, 4,4'-dimethoxybenzoin, 4-chlorobenzoin, benzyl 4-hydroxyphenyl ketone, benzyl 2,4-dihydroxyphenyl ketone, 2-phenyl-2',4',6'-trihydroxyacetophenone.

5. The coating of claim 1 wherein the diaryl ketone monomer comprises a polymerizable group selected from the group consisting of acrylate groups, methacrylate groups, and methylmethacrylate groups.

6. The coating of claim 1 wherein the plurality of monomers further comprises one or more monomers selected from the group consisting of poly(ethylene glycol) methacrylate, poly(propylene glycol) methacrylate, poly(ethylene glycol) methyl ether methacrylate, poly(ethylene glycol) ethyl ether methacrylate, 3-trimethoxysilyl propyl methacrylate, vinyl sulfonic acid (sodium salt), ammonium sulfatoethyl methacrylate, 2-acryloylamido-2-methylpropanesulfonic acid monomer, [2-(methacryloyloxy)ethyl] dimethyl-(3-sulfopropyl)ammonium hydroxide (MEDSAH), [3-(methacryloylamino)propyl]dimethyl-(3-sulfopropyl)ammonium hydroxide (MPDSAH), 2-methacryloyloxyethyl phopshorylcholine (MPC), acrylic acid (sodium salt), dimethylaminoethyl methacrylate, 2-hydroxyethyl methacrylate (HEMA), polyhexanide methacrylate and chlorhexidine methacrylate.

7. The coating of claim 1 wherein the plurality of monomers further comprises a monomer that comprises a polyethylene glycol pendant group.

8. The coating of claim 1 wherein the plurality of monomers further comprises a monomer that comprises a pendant group terminating in a sulfonate group.

9. The coating of claim 1 wherein the plurality of monomers further comprises a monomer that comprises a silyl pendant group.

10. The coating of claim 1 wherein the plurality of monomers further comprise a monomer that comprises a zwitterionic group.

11. The coating of claim 1 wherein the plurality of monomers further comprise a monomer that comprises a hydroxyl group.

12. The coating of claim 1 wherein the copolymers, before photoinitiation, consist essentially of the polymerization product of the N-vinyl pyrrolidinone and the diaryl ketone monomer.

13. The coating of claim 1 wherein the medical device is selected from the group consisting of a stent, a guidewire, a pacemaker lead, a catheter, a medical balloon, a nasogastric feeding tube, and an endotracheal tube.

14. The coating of claim 1 wherein the monomers comprise an n-alkyl methacrylate monomer.

15. The coating of claim 14 wherein the n-alkyl methacrylate monomer is butyl methacrylate and the monomers comprise methoxypolyethylene glycol methacrylate.

16. A coating on a medical device comprising
a hydrophilic layer comprising copolymers covalently crosslinked by photoinitiation of diaryl ketones pendant on the copolymers,
with the copolymers, before photoinitiation, being polymerized from a plurality of monomers comprising N-vinyl pyrrolidinone and diaryl ketone vinyl monomer, having a weight average molecular weight of more than about 100,000, at least about 60% by weight N-vinyl pyrrolidinone, no more than about 5% by weight of diaryl ketone monomer that provides the pendant diaryl ketones, and a random distribution of the diaryl ketones,
wherein the copolymers, before photoinitiation, consist essentially of the polymerization product of the N-vinyl pyrrolidinone and the diaryl ketone monomer.

17. A coating on a medical device comprising
a hydrophilic layer comprising copolymers covalently crosslinked by photoinitiation of diaryl ketones pendant on the copolymers,
with the copolymers, before photoinitiation, being polymerized from a plurality of monomers comprising N-vinyl pyrrolidinone and diaryl ketone vinyl monomer, having a weight average molecular weight of more than about 100,000, at least about 60% by weight N-vinyl pyrrolidinone, no more than about 5% by weight of diaryl ketone monomer that provides the pendant diaryl ketones, and a random distribution of the diaryl ketones,
wherein the plurality of monomers comprises a monomer that comprises a pendant group chosen from the group consisting of polyethylene glycol, a silyl pendant group, a zwitterionic group, a hydroxyl group, and a pendant group terminating in a sulfonate group.

18. The coating of claim 17, wherein the coating has a friction coefficient of no more than about 0.2.

19. The coating of claim 17 wherein the diaryl ketone is benzophenone.

20. The coating of claim 17 wherein the diaryl ketone monomer comprises a polymerizable group selected from the group consisting of acrylate groups, methacrylate groups, and methylmethacrylate groups.

21. The coating of claim 17 wherein the plurality of monomers comprises the monomer that comprises the polyethylene glycol pendant group.

22. The coating of claim 17 wherein the plurality of monomers comprises the monomer that comprises the pendant group terminating in a sulfonate group.

23. The coating of claim 17 wherein the plurality of monomers comprises the monomer that comprises the silyl pendant group.

24. The coating of claim 17 wherein the plurality of monomers comprises the monomer that comprises the zwitterionic group.

25. The coating of claim 17 wherein the plurality of monomers comprises the monomer that comprises the hydroxyl group.

26. The coating of claim 17 wherein the medical device is selected from the group consisting of a stent, a guidewire, a pacemaker lead, a catheter, a medical balloon, a nasogastric feeding tube, an endotracheal tube a PICC line, and a surface exposed to blood.

27. A coating on a medical device comprising
a hydrophilic layer comprising copolymers covalently crosslinked by photoinitiation of diaryl ketones pendant on the copolymers,
with the copolymers, before photoinitiation, being polymerized from a plurality of monomers comprising N-vinyl pyrrolidinone and diaryl ketone vinyl monomer, having a weight average molecular weight of more than about 100,000, at least about 60% by weight N-vinyl pyrrolidinone, no more than about 5% by weight of diaryl ketone monomer that provides the pendant diaryl ketones, and a random distribution of the diaryl ketones,
wherein the medical device is selected from the group consisting of a stent, a guidewire, a pacemaker lead, a catheter, a medical balloon, a nasogastric feeding tube, an endotracheal tube a PICC line, and a surface exposed to blood.

28. The coating of claim 27, wherein the coating has a friction coefficient of no more than about 0.2.

29. The coating of claim 27 wherein the diaryl ketone is benzophenone.

30. The coating of claim 27 wherein the diaryl ketone monomer comprises a polymerizable group selected from the group consisting of acrylate groups, methacrylate groups, and methylmethacrylate groups.

31. The coating of claim 27 wherein the plurality of monomers comprises a monomer that comprises a polyethylene glycol pendant group.

32. The coating of claim 27 wherein the plurality of monomers comprises a monomer that comprises a pendant group terminating in a sulfonate group.

33. The coating of claim 27 wherein the plurality of monomers comprises a monomer that comprises a silyl pendant group.

34. The coating of claim 27 wherein the plurality of monomers comprises a monomer that comprises a zwitterionic group.

35. The coating of claim 27 wherein the plurality of monomers comprises a monomer that comprises a hydroxyl group.

36. The coating of claim 27 wherein the monomers comprise an n-alkyl methacrylate monomer.

37. The coating of claim 36 wherein the n-alkyl methacrylate monomer is butyl methacrylate and the monomers comprise methoxypolyethylene glycol methacrylate.

* * * * *